(12) United States Patent
Hotta

(10) Patent No.: US 9,315,777 B2
(45) Date of Patent: Apr. 19, 2016

(54) CULTURE MEDIUM AND METHOD FOR INDUCING DIFFERENTIATION INTO BONE CELLS

(75) Inventor: Yoshiyuki Hotta, Tokyo (JP)

(73) Assignee: FUJIREBIO INC., Tokyo (JP)

( * ) Notice: Subject to any disclaimer, the term of this patent is extended or adjusted under 35 U.S.C. 154(b) by 439 days.

(21) Appl. No.: 13/202,713

(22) PCT Filed: Feb. 18, 2010

(86) PCT No.: PCT/JP2010/052455
§ 371 (c)(1), (2), (4) Date: Aug. 22, 2011

(87) PCT Pub. No.: WO2010/095685
PCT Pub. Date: Aug. 26, 2010

(65) Prior Publication Data
US 2011/0306132 A1    Dec. 15, 2011

(30) Foreign Application Priority Data

Feb. 23, 2009  (JP) ................................. 2009-038998

(51) Int. Cl.
*C12N 5/077*    (2010.01)

(52) U.S. Cl.
CPC .......... *C12N 5/0654* (2013.01); *C12N 2500/25* (2013.01); *C12N 2500/36* (2013.01); *C12N 2500/38* (2013.01); *C12N 2500/42* (2013.01); *C12N 2501/39* (2013.01)

(58) Field of Classification Search
None
See application file for complete search history.

(56) References Cited

FOREIGN PATENT DOCUMENTS

| EP | 1 988 169 A1 | 11/2008 |
|---|---|---|
| EP | 2233565 A1 * | 9/2010 |
| JP | 2007340802 * | 12/2007 |
| WO | WO 03/104442 A1 | 12/2003 |

OTHER PUBLICATIONS

Panupinthu, Nattapon; et al; "P2X7 receptors on osteoblasts couple to production of lysophosphatidic acid: a signaling axis promoting osteogenesis" Journal of Cell Biology, 181, 859-871, 2008.*

Atkins et al., "Human Trabecular Bone-Derived Osteoblasts Support Human Osteoclast Formation In Vitro in a Defined, Serum-Free Medium", Journal of Cellular Physiology, vol. 203, pp. 573-582, 2005.
Freitas et al., "Fluoroaluminate Stimulates Phosphorylation of p130 Cas and Fak and Increases Attachment and Spreading of Preosteoblastic MC3T3-E1 Cells", Bone, vol. 30, No. 1, pp. 99-108, Jan. 2002.
Lee et al., "Development of a Serum-free Medium for the Production of Erythropoietin by Suspension Culture of Recombinant Chinese Hamster Ovary Cells Using a Statistical Design", Journal of Biotechnology, vol. 69, pp. 85-93, 1999.
Saito et al., "Proceedings of Japanese Conference on the Biochemistry of Lipids", vol. 45, pp. 262-265, May 15, 2005.
Sanchez-Hidalgo et al., "Melatonin Inhibits Fatty Acid-Induced Triglyceride Accumulation in ROS17/2.8 Cells: Implications for Osteoblast Differentiation and Osteoporosis", Am. J. Physiol. Regul. Integr. Comp. Physiol., vol. 292, pp. R2208-R2215, 2007.
Yeum et al., "Effects of Vitamin K2 on Adipogenic and Osteogenic Differentiation in Mesenchymal Stem Cells from Human Umbilical Cord Blood", Key Engineering Materials, vols. 342-343, pp. 121-124, 2007.
European Search Report for European Application No. 10743811.1, dated Nov. 25, 2013.
Pebay et al., "Essential Roles of Sphingosine-1-Phosphate and Piatslet-Derived Growth Factor in the Maintenance of Human Embryonic Stem Cells,", Stem Cells, vol. 23, pp. 1541-1548, 2005.

* cited by examiner

*Primary Examiner* — Renee Claytor
*Assistant Examiner* — David Berke-Schlessel
(74) *Attorney, Agent, or Firm* — Birch, Stewart, Kolasch & Birch, LLP.

(57) ABSTRACT

Disclosed are a culture medium, an additive, and a method for efficiently inducing the differentiation of mammalian somatic stem cells into cells having the characteristics of bone cells under conditions of serum-free or low-serum culture medium. The culture medium for inducing the differentiation of mammalian somatic stem cells into bone cells comprises a basal medium for culturing mammalian cells, an agent for inducing the differentiation of mammalian somatic stem cells into bone cells, a ligand for endothelial cell differentiation gene (Edg) family receptors and selenium, which culture medium is serum-free or contains a low concentration of serum. The method for inducing differentiation from somatic stem cells into bone cells comprises culturing the somatic stem cells that can differentiate into bone cells in the above-described culture medium.

5 Claims, 3 Drawing Sheets

Human bone marrow-derived mesenchymal stem cells

Alkaline phosphatase activity

1: Conventional culture medium (Comparative Example 2)
2: Conventional differentiation culture medium (Comparative Example 3)
3: Serum-free control culture medium (Comparative Example 1)
4: Serum-free differentiation culture medium (Example 1)

CULTURE MEDIUM AND METHOD FOR INDUCING DIFFERENTIATION INTO BONE CELLS

TECHNICAL FIELD

The present invention relates to a culture medium and a method for inducing the differentiation of mammalian somatic stem cells or osteoblast cells into bone cells under conditions of serum-free or low-serum culture medium.

BACKGROUND ART

Researches of regenerative medicine, cell transplantation and the like have started wherein human somatic stem cells or the like are cultured in a culture room under a clean environment and the cultured stem cells are transplanted into human body, to attain regeneration of damaged sites and therapy of diseases, and practice of these techniques have also started.

For maintenance-culturing human somatic stem cells used for the therapy and induction to differentiated cells (e.g., bone cells, adipocytes, myocardial cell and the like), an animal serum (e.g., fetal bovine serum, human serum or the like) is used. However, the composition of the animal serum is not fully clarified, and it is known that there is a risk that the animal serum may be infected by an unknown virus or prion.

Further, it is known that the growth ability of the cultured cells and performances such as differentiation inducing ability vary depending on the origin or product lot of the animal serum. Therefore, there is a problem in that it is difficult to attain constant performance of the maintenance culturing and constant quality of the differentiation-induced cells cultured in a medium containing a high concentration of an animal serum.

To avoid the risk of infection by an unknown virus or prion, the serum of the patient who is necessary to receive the cell transplantation is used in place of an animal serum in order to avoid the risk that the animal serum may be infected by an unknown virus or prion. However, in cases where the serum of the patient is used, it is necessary to collect a relatively large amount of blood from the patient, so that the physical burden of the patient is large, which is problematic.

In recent years, to make the influence by the origin of the animal serum or lot as small as possible, methods for differentiation induction in a medium containing a reduced amount of serum is used have been reported. For example, a method of differentiation induction of bone cells from mesenchymal stem cells wherein the amount of the added serum is reduced (Non-Patent Literature 1). Non-Patent Literature 1 is directed to an invention wherein mesenchymal stem cells originated from human bone marrow cells are cultured in a medium containing human serum, and discloses an example wherein the cultured human mesenchymal cells originated from human bone marrow cells are induced to a bone tissue in a differentiation induction medium containing human serum.

In the conventional methods of differentiation induction to bone cells from mesenchymal stem cells, β-glycerophosphate, dexamethasone, vitamin C and 10% animal serum are added (Non-Patent Literature 2).

Further, Non-Patent Literature 2 discloses a serum-free medium for culturing human embryonic stem (ES) cells, comprising a ligand for lysophospholipid receptor, that is, a ligand for endothelial cell differentiation gene (Edg) family receptors, such as lysophosphatidic acid (LPA), sphingosine 1-phosphate (S1P) or the like.

PRIOR ART REFERENCES

Patent Literatures

[Patent Literature 1] JP 2006-55106 A
[Patent Literature 2] Japanese Translated PCT Patent Application Laid-open No. 2006-505248

Non-Patent Literatures

[Non-Patent Literature 1] BMC Mol. Biol. 2008 Feb. 26; 9:26
[Non-Patent Literature 2] J. Cell. Biochem. Vol. 64, 295-312 (1997)

SUMMARY OF THE INVENTION

Problem to be Solved by the Invention

An object of the present invention is to provide a culture medium, an additive, and a method for inducing differentiation of mammalian somatic stem cells into cells having characteristics of bone cells under serum-free or low-serum conditions.

Means for Solving the Problem

As a result of an intensive study, the present inventors discovered that mammalian somatic stem cells can be effectively differentiated into bone cells in a serum-free medium containing lysophosphatidic acid which is a ligand for endothelial cell differentiation gene (Edg) family receptors and selenium which is a trace element, in addition to the agent for induction to bone cells from mammalian somatic cells, which agent is conventionally added. Further, the present inventors discovered that melatonin, vitamin D, vitamin A, vitamin K and zinc which are involved in the differentiation from somatic stem cells into bone cells, can be further added to this serum-free medium, thereby completing the present invention.

That is, the present invention provides a culture medium for inducing the differentiation of mammalian somatic stem cells into bone cells, comprising a basal medium for culturing mammalian cells, an agent for inducing differentiation of mammalian somatic stem cells into bone cells, a ligand for endothelial cell differentiation gene (Edg) family receptors, and selenium, which culture medium is serum-free or contains a low concentration of serum. The present invention also provides an additive to a culture medium for inducing the differentiation of mammalian somatic stem cells into bone cells, the additive comprising a ligand for endothelial cell differentiation gene (Edg) family receptors and selenium. The present invention further provides a method for inducing differentiation of somatic stem cells into bone cells, the method comprising culturing the somatic stem cells that can differentiate into bone cells in the above-described culture medium according to the present invention.

Effects of the Invention

The culture medium and the additive thereto according to the present invention enable mammalian somatic stem cells to be effectively induced to differentiated into osteocytes under the conditions of not using animal serum added to conventional differentiation inducing culture media when inducing the differentiation of mammalian somatic stem cells into osteocytes, that is, under serum-free conditions. In addition, the present invention can eliminate the problems, which is influences of the origin and lot of serum on differentiation-induction, invasion of known or unknown infectious pathogen and the like, caused by use of serum. As a result, osteocytes with stable quality can be obtained.

MODE FOR CARRYING OUT THE INVENTION

Figure 1:
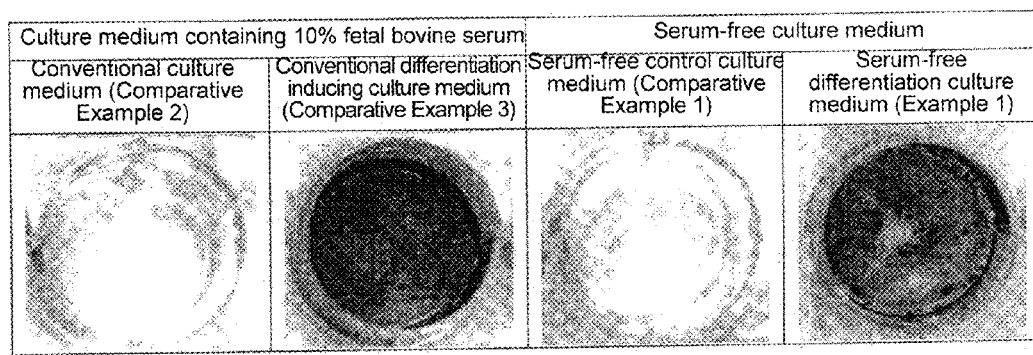
FIG. 1 shows the cells stained with alizarin red S, which cells were differentiation-induced into bone cells from mesenchymal stem cells originated from human bone marrow cells, in each of the media obtained in Example 1 and Comparative Examples 1 to 3 for 21 days.

In the present invention, "somatic stem cells" are cells capable of transdifferentiating into one or more kinds of tissue cells forming each organ in vivo, such as osteoblasts, adipocytes, chondrocytes, skin cells, nerve cells, muscle cells, blood cells, fibroblasts, and hepatocytes. Additionally, the "somatic stem cells" are cells except embryonic stem cells in stem cells and precursor cells with the ability to differentiate into cells having some different kinds of functions, such as induced multipotent stem cells, hematopoietic stem cells, mesenchymal stem cells, neural stem cells, skin stem cells, hepatic stem cells, and pancreatic stem cells.

There is no restriction on cells that can be differetiation-induced in the culture medium of the present invention, as long as the cells are somatic stem cells, which can be induced to differentiate into osteocytes. Preferable examples of the cells include somatic stem cells such as mesenchymal stem cells derived from fibrocytes and adipose tissue-derived stem cells and the like, although not restricted thereto.

The culture medium according to the present invention includes, as an essential component, a ligand for endothelial cell differentiation gene (Edg) family receptors. The Edg family receptors are a group of G protein-coupled receptors sharing a high degree of gene sequence homology, and receptors Edg-1 through Edg-8 have been identified to date in mammals such as humans, mice, and sheep. Among them, Edg-2, Edg-4, and Edg-7 are known to serve as LPA receptors and Edg-1, Edg-3, Edg-5, Edg-6, and Edg-8 are known to serve as SIP receptors. Additionally, "a ligand for receptors" means a substance coupled specifically to the receptors and includes not only natural ligands existing in vivo but also other natural or synthesized compounds known as agonists and antagonists.

The ligand for Edg family receptors (hereinafter referred to as "Edg ligand") is preferably one or more kinds of compounds selected from the group consisting of agonists such as lysophosphatidic acid (LPA) and a salt thereof.

The agonists for Edg family receptors are substances that couple to Edg family receptors to act like LPA. Examples of the agonists include sphingosine 1-phosphate (SIP), dihydrosphingosine 1-phosphate, platelet-activating factor (PAF), sphingosylphosphorylcholine, alkyl LPA analogues, and FTY 720.

LPA is a compound represented by the following general formula (I):

$$R-O-CH_2CH(OH)CH_2PO_4H_2 \quad (I)$$

(wherein R represents a $C_{10}$-$C_{30}$ alkyl group, a $C_{10}$-$C_{30}$ alkenyl group, or a $C_{10}$-$C_{30}$ acyl group). The carbon number of the acyl group as the R group in the above formula (I) does not include the carbon number of carbonyl group.

The salt of LPA may be a conventionally known salt, and examples of the salt of LPA include alkali metal salts such as sodium salt and potassium salt, and ammonium salts. As LPA or the salt thereof, there may be mentioned 1-oleoyl lysophosphatidic acid sodium salt, LPA potassium salt, and the like.

The Edg ligands may be used alone or in combination of two or more kinds thereof.

The medium of the present invention contains selenium which is a trace element. It is known that selenium plays an important role in the activity of glutathione peroxidase which decomposes hydrogen peroxide generated in cells into water and oxygen.

Selenium is usually contained in the medium in the form of a compound such as selenic acid or sodium selenite.

Such a selenium-containing compound may be used individually, or 2 or more of the compounds may be used in combination.

The concentration of the Edg ligand in the medium of the present invention is preferably from 0.01 μM to 50 μM, more preferably 0.1 μM to 10 μM. The concentration of selenium is preferably 1 nM to 1 μM, more preferably 1 nM to 500 nM.

The medium may also contain at least one selected from the group consisting of vitamin A, vitamin D and vitamin K which are fat-soluble vitamins, melatonin which is a pineal hormone and zinc which is a trace element. Vitamin A is known to control induction of differentiation from embryonic stem cells to nerve cells. Vitamin K is known to have an activity to coagulate blood and an activity to deposit calcium onto bones. Melatonin is known to have an activity to inhibit differentiation from somatic stem cells into adipocytes and to show circadian rhythm as a pineal hormone and to be involved in sleeping. Zinc is an essential trace element and is known to be necessary for activities of many enzymes.

Examples of vitamin A include retinoic acid and derivatives thereof. Vitamin A may be used individually or two or more of these may be used in combination. In cases where vitamin A is contained in the medium, the concentration is not restricted, and is usually about 0.1 μM to 100 μM, preferably about 1 μM to 10 μM.

Examples of vitamin D include ergocalciferol, cholecalciferol, derivatives thereof (e.g., 7-dehydrocholesterol and the like) and metabolites thereof (e.g., calcitriol). Vitamin D may be used individually or two or more of these may be used in combination. In cases where vitamin D is contained in the medium, the concentration is not restricted, and is usually about 0.1 nM to 500 nM, preferably about 1 nM to 100 nM.

Examples of vitamin K include phylloquinone, menaquinone, menadione and menadiol sodium diphosphate. Vitamin K may be used individually or two or more of these may be used in combination. In cases where vitamin K is contained in the medium, the concentration is not restricted, and is usually about 0.1 μM to 100 μM, preferably about 1 μM to 10 μM.

In cases where melatonin is contained in the medium, the concentration is not restricted, and is usually about 0.1 nM to 100 nM, preferably about 1 nM to 50 nM.

Zinc may be added to the medium in the form of a zinc compound. Examples of such a zinc compounds include zinc chloride ($ZnCl_2$), zinc oxide (ZnO), zinc sulfide (ZnS) and zinc sulfate ($ZnSO_4$). These zinc compounds may be used individually or two or more of these may be used in combination. In cases where zinc is contained in the medium, the concentration is not restricted, and is usually about 0.1 nM to 100 µM, preferably about 1 n M to 10 µM.

The medium of the present invention contains an agent for inducing differentiation of mammalian somatic cells into bone cells. Agents for inducing differentiation of mammalian somatic cells into bone cells per se are known, and known differentiation-inducing agents may preferably used in the present invention. Preferred examples of the known differentiation-inducing agents include those simultaneously containing β-glycerophosphate, dexamethasone and vitamin C.

Vitamin C is known as a water-soluble vitamin. Vitamin C is used for biosynthesis of amino acids and is also known for its important role in hydroxylation reactions proceeding in vivo, such as the secretion of hormone from the adrenal gland, the synthesis of L-carnitine as a carrier that transports fatty acids to mitochondria, and the production of collagen in connective tissue. Vitamin C may be ascorbic acid, ascorbic acid 2-phosphate or a salt thereof, or a mixture thereof.

The concentration of the differentiation-inducing agent is appropriately selected depending on the type of the differentiation-inducing agent and the type of the cells, and in cases where the differentiation-inducing agent simultaneously contains β-glycerophosphate, dexamethasone and vitamin C, the concentration of β-glycerophosphate is preferably from 1 mM to 100 mM, more preferably 5 mM to 50 mM, the concentration of dexamethasone is preferably from 1 nM to 1 µM, more preferably 10 nM to 500 nM, and the concentration of vitamin C is preferably from 10 µM to 10 mM, more preferably from 200 µM to 2 mM.

The culture medium of the present invention may be the same as a known mammalian cell culture medium except that the culture medium includes the above-described two kinds of essential components and the above-described differentiation inducing substance. Accordingly, the culture medium of the present invention can be obtained by adding to the known basal medium the above-described two kinds of essential components and the differentiation inducing agent conventionally used for inducing differentiation into osteocytes.

Preferable examples of a known serum-free basal medium that can be used for the culture medium of the present invention include minimum essential medium (MEM) such as Eagle's culture medium, Dulbecco's modified Eagle's medium (DMEM), minimum essential medium alpha (MEM-alpha), mesenchymal cell basal medium (MSCBM), Ham's F-12 medium and Ham's F-10 medium, DMEM/F12 medium, William's medium E, RPMI-1640 medium, MCDB medium, medium 199, Fisher's medium, Iscove's modified Dulbecco's medium (IMDM), and McCoy's modified medium. These culture media are all those known in this field.

The culture medium of the present invention may further include various additives that are known to be included in mammalian cell culture media. As examples of such known additives, there may be mentioned amino acids, inorganic salts, vitamins, and other additives such as carbon sources and antibiotics.

As the amino acids, there may be mentioned glycine, L-alanine, L-arginine, L-asparagine, L-aspartic acid, L-cysteine, L-cystine, L-glutamic acid, L-glutamine, L-histidine, L-isoleucine, L-leucine, L-lysine, L-methionine, L-phenylalanine, L-proline, L-serine, L-threonine, L-tryptophan, L-tyrosine, and L-valine.

As the inorganic salts, there may be mentioned calcium chloride, copper sulfate, iron (III) nitrate, iron sulfate, magnesium chloride, magnesium sulfate, potassium chloride, sodium hydrogen carbonate, sodium chloride, disodium hydrogenphosphate, sodium dihydrogenphosphate, and zinc sulfate.

As the vitamins, there may be mentioned choline, vitamin A, vitamin B1, vitamin B2, vitamin B3, vitamin B4, vitamin B5, vitamin B6, Vitamin B7, vitamin B12, vitamin B13, vitamin B15, vitamin B17, vitamin Bh, vitamin Bt, vitamin Bx, vitamin D, vitamin E, vitamin F, vitamin K, vitamin M, and vitamin P.

The addition of these additives to a mammalian cell culture medium per se is known. The quantity of each additive to be added may also be the same as that in a known culture medium and can be appropriately determined by routine testing. For example, the quantity of the amino acids to be added ranges usually about from 5 mg/L to 500 mg/L for each amino acid, and preferably about from 10 mg/L to 400 mg/L; the quantity of the inorganic salts to be added ranges usually from about 0 mg/L to 10 g/L, and preferably from about 0.01 mg/L to 7 g/L; and the quantity of the vitamins to be added ranges from about 0.01 mg/L to 500 mg/L for each vitamin, and preferably from about 0.05 mg/L to 300 mg/L.

As other additives, there may be mentioned (1) growth factors such as fibroblast growth factor (FGF), endothelial growth factor (EGF), and platelet-derived growth factor (PDGF), (2) antibiotics such as penicillin, streptomycin, gentamicin, and kanamycin, (3) carbon sources such as glucose, galactose, fructose, and sucrose, (4) trace metals such as magnesium, iron, zinc, calcium, potassium, sodium, copper, selenium, cobalt, tin, molybdenum, nickel, and silicon, (5) antioxidants such as 2-mercaptoethanol, catalase, superoxide dismutase, and N-acetylcysteine, and other additives such as adenosine 5'-monophosphate, corticosterone, ethanolamine, insulin, reduced glutathione, lipoic acid, hypoxanthine, phenol red, progesterone, putrescine, pyruvic acid, thymidine, triiodothyronine, transferrin, and lactoferrin. The quantities of these additives to be added may also be the same as those in the conventional art, and can also be appropriately determined by routine testing in accordance with the purpose of each additive. The quantity of each additive ranges usually about from 0.001 mg/L to 5 g/L, and particularly about from 0.1 to 3 g/L.

The culture medium of the present invention can include one or more kinds of the various additives described above and usually includes a combination of plural kinds of additives.

Among the other additives, glutamic acid is preferable since it is thought to exhibit an effect of cell viability and differentiation into osteocytes when added to the culture medium. The preferable concentration of glutamic acid in the culture medium ranges about from 1 µM to 10 mM, and more preferably about from 25 µM to 250 µM.

The culture medium of the present invention is serum-free or contains a low concentration of serum, and preferably it is serum-free. In this case, the culture medium with "a low concentration of serum" means the culture medium that contains serum whose content is 5% by weight or lower, and preferably 1% by weight.

In the culture medium of the present invention, culturing of mammalian somatic cells per se can be conducted in the same manner as the conventional art and is usually conducted at a temperature of 30 to 37 degrees C. under the environments of 5% $CO_2$ and 5 to 21% $O_2$. In addition, culturing time required for differentiation induction can be appropriately determined by the kinds of the differentiation inducing agent, the cells, and the like to be used, and also can be appropriately determined by observing the conditions of the cells. Usually, the culturing time ranges about from 10 days to 30 days.

The present invention also provides an additive for forming the above-described culture medium of the present invention. Thus, the additive according to the present invention includes the above-described Edg ligand, and selenium. In addition to them, the additive of the present invention may further include the above-described differentiation inducing agent. Furthermore, the additive may include one or more kinds of the additives described above. Still furthermore, the additive may contain the component of the basal medium so as to provide the culture medium of the present invention by being merely dissolved in water. Conveniently and preferably, the additive of the present invention has a composition that provides the above-described culture medium of the present invention by being dissolved in water or the basal medium. In this case, the mixing ratio of each component contained in the additive is the same as the ratio of the content of each component in the culture medium. As the basal medium, there may be mentioned the above-described various culture media that are conventionally used for culturing mammalian cells.

Hereinafter, the present invention will be explained in more detail based on Examples and Comparative Examples, although the invention is not restricted to the Examples below. Concentrations mentioned in each Example are the final concentrations in the culture medium. The lysophosphatidic acid (LPA) used was all 1-oleoyl lysophosphatidic acid sodium, and the selenium compound was all sodium selenite.

EXAMPLES

Example 1 and Comparative Examples 1 to 3

Induction of Differentiation from Mesenchymal Stem Cells Originated from Human Bone Marrow into Bone Cells under Serum-free Conditions 1

To a basal medium (DMEM), 5 µM of lysophosphatidic acid (LPA), 1 mM of ascorbic acid 2-phosphate and 60 nM of selenide were added to obtain a serum-free control medium (Comparative Example 1).

To DMEM, 10 mM of β-glycerophosphate, 100 nM of dexamethasone and 200 µM of ascorbic acid phosphate, the concentrations being final concentrations, were added to prepare a bone cell differentiation-induction basal medium (differentiation basal medium). To this bone cell differentiation-induction basal medium, 5 µM of LPA, 1 mM of ascorbic acid 2-phosphate, 60 nM of selenide and 90 µM of glutamic acid were added to prepare a serum-free differentiation medium according to the present invention (Example 1).

To each of DMEM and the differentiation basal medium, 10% of fetal bovine serum (FBS) was added to produce a conventional culture medium (Comparative Example 2) and a conventional differentiation culture medium (Comparative Example 3).

Human bone marrow-derived mesenchymal stem cells (strain name: normal human mesenchymal stem cells (Cryo hMSC purchased from LONZA) were seeded in a well with a 12-hole culture plate at a cell density of 10,000 cells/cm$^2$ to culture the cells at 37 degrees C. and 5% $CO_2$ for 7 to 21 days in the above-described each media, thereby inducing differentiation into osteocytes.

Bone cells were confirmed by staining with alizarin red S. The alkaline phosphatase (ALP) activity of the cells was determined by TRACP&ALP Assay Kit (produced by Takara Bio). The expression level of mRNA of ALP was determined by the real-time PCR method. The used primers were as follows: ALP: forward primer: (cgtatttctccagacccagagg (SEQ ID NO: 1), reverse primer: (ggccttgtcctgaggagaaaga, SEQ ID NO:2). The results are shown in FIGS. 1 to 3.

Figure 2:
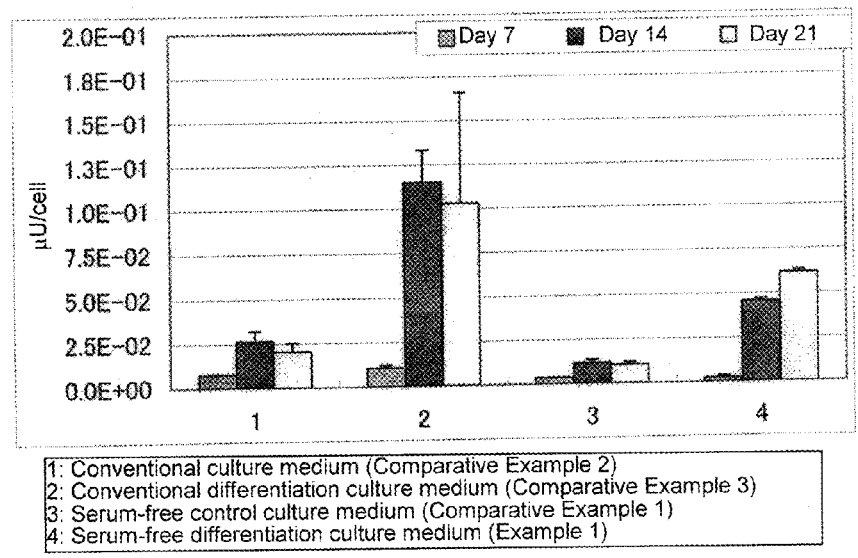
FIG. 2 is a graph showing the change in ALP activity of the cells which were differentiation-induced into bone cells from mesenchymal stem cells originated from human bone marrow cells, in each of the media obtained in Example 1 and Comparative Examples 1 to 3 for 7 to 21 days.
Figure 3:
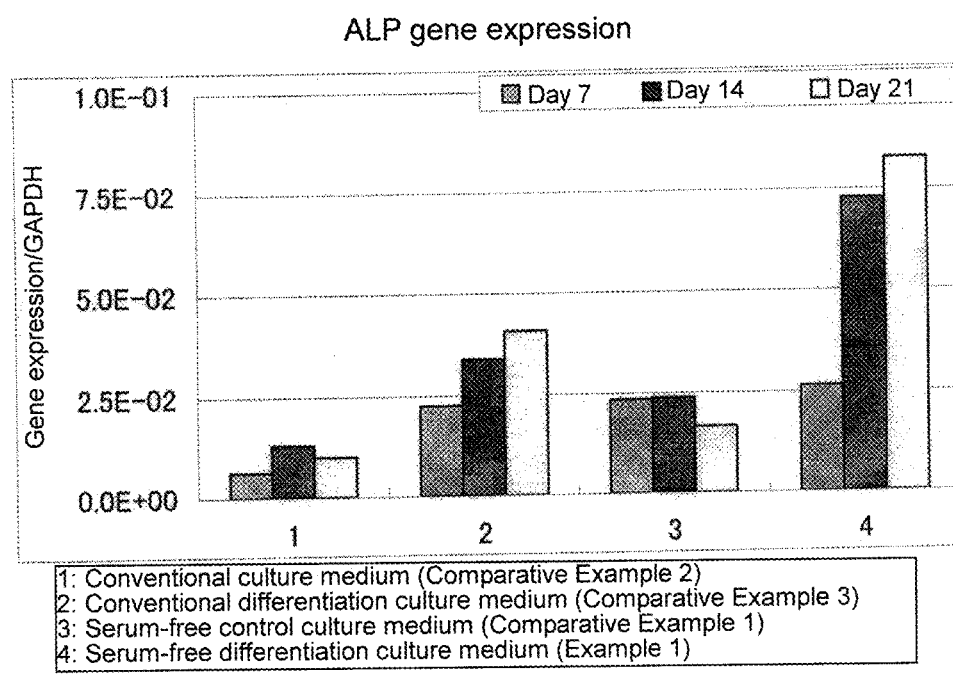
FIG. 3 is a graph showing the change in expression level of mRNA of ALP of the cells which were differentiation-induced into bone cells from mesenchymal stem cells originated from human bone marrow cells, in each of the media obtained in Example 1 and Comparative Examples 1 to 3 for 7 to 21 days.

As shown in FIGS. 1 to 3, and as can be seen from the results of alizarin red S staining, differentiation from the mesenchymal stem cells originated from bone marrow into bone cells was confirmed. The percentage of the induced bone cells was about the same as that attained using the conventional differentiation medium containing serum (Comparative Example 3).

Example 2 and Comparative Examples 4 to 9

Induction of Differentiation from Mesenchymal Stem Cells Originated from Human Bone Marrow into Bone Cells Under Serum-Free Conditions 2

As in Example 1, a serum-free control medium A (Comparative Example 4) was prepared by adding to a basal medium (DMEM) 5 µM of LPA, 1 mM of ascorbic acid 2-phosphate and 100 nM of selenide.

As in Example 1, to DMEM, 10 mM of β-glycerophosphate, 100 nM of dexamethasone and 200 µM of ascorbic acid phosphate, the concentrations being final concentrations, were added to prepare a bone cell differentiation-induction basal medium (differentiation basal medium). To this bone cell differentiation-induction basal medium as in Example 1, 5 µM of LPA, 1 mM of ascorbic acid 2-phosphate, 100 nM of selenide and 90 µM of glutamic acid were added to prepare a serum-free differentiation medium according to the present invention (Example 2-1).

To DMEM, 5 µM of LPA, 1 mM of ascorbic acid 2-phosphate, 100 nM of selenide, 50 nM of cholecalciferol and 5 nM of melatonin were added to prepare a serum-free control medium B (Comparative Example 5). To DMEM, 5 µM of LPA, 1 mM of ascorbic acid 2-phosphate, 100 nM of selenide, 50 nM of cholecalciferol and 2.5 µM of vitamin A acetate were added to prepare a serum-free control medium C (Comparative Example 6). To DMEM, 5 µM of LPA, 1 mM of ascorbic acid 2-phosphate, 100 nM of selenide, 50 nM of cholecalciferol and 1 µM of vitamin K3 were added to prepare a serum-free control medium D (Comparative Example 7).

To the differentiation basal medium, 5 µM of LPA, 1 mM of ascorbic acid 2-phosphate, 100 nM of selenide, 50 nM of cholecalciferol and 5 nM of melatonin were added to prepare a serum-free differentiation medium B (Example 2-2). To DMEM, 5 µM of LPA, 1 mM of ascorbic acid 2-phosphate, 100 nM of selenide, 50 nM of cholecalciferol and 2.5 µM of vitamin A acetate were added to prepare a serum-free differentiation medium C (Example 2-3). To DMEM, 5 µM of LPA, 1 mM of ascorbic acid 2-phosphate, 100 nM of selenide, 50 nM of cholecalciferol and 1 µM of vitamin K3 were added to prepare a serum-free differentiation medium D (Example 2-4).

To DMEM and the differentiation basal medium, respectively, 10% fetal bovine serum (FBS) was added to prepare a conventional medium (Comparative Example 8) and conventional differentiation medium (Comparative Example 9).

As in Example 1, mesenchymal stem cells originated from human bone marrow were plated on the wells of a 12-well culture plate to a cell population of 3000 cells/cm$^2$, and the cells were cultured in each of these media at 37° C., under 5% $CO_2$ for 21 days, to induce differentiation into bone cells. Bone cells were confirmed by staining with alizarin red S.

Figure 4:
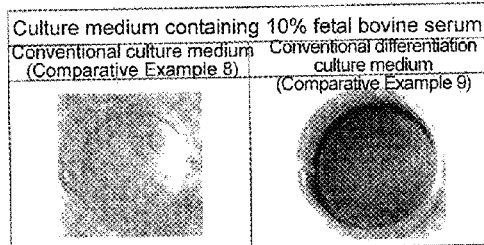
FIG. 4 shows the cells stained with alizarin red S, which cells were differentiation-induced into bone cells from mesenchymal stem cells originated from human bone marrow cells, in each of the media obtained in Example 2 and Comparative Examples 4 to 6 for 14 days.
Figure 4:
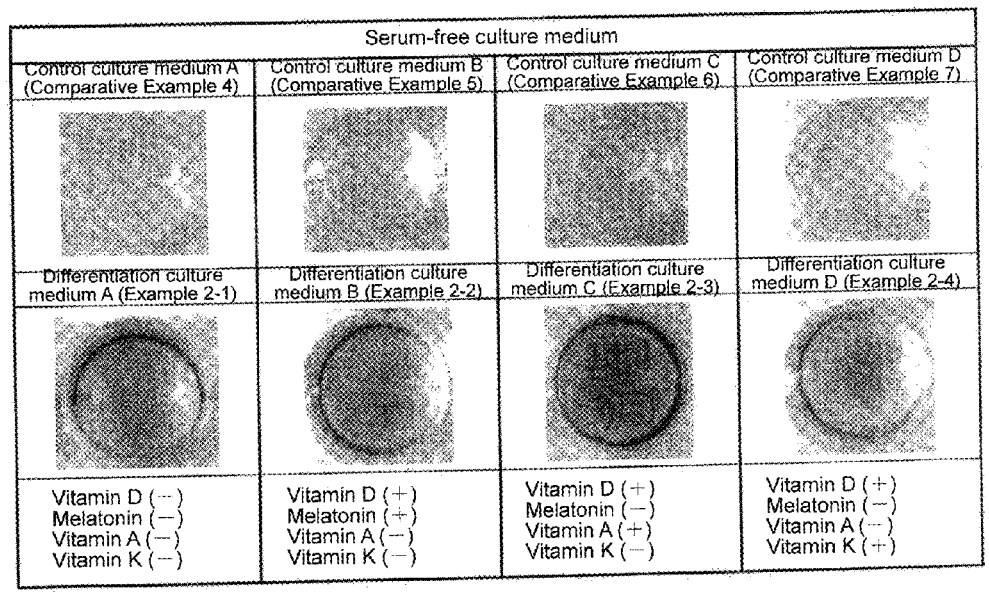

The results are shown in FIG. 4. As shown in FIG. 4, by using the serum-free differentiation media B to D which were prepared by combining the serum-free differentiation medium A with cholecalciferol, melatonin, vitamin A acetate, or vitamin K3, differentiation into bone cells was confirmed to the extent similar to the case where the conventional serum-containing differentiation medium (Comparative Example 9) was used. It was confirmed that differentiation into bone cells was not attained by using the conventional medium (Comparative Example 8), or serum-free control media A to D (Comparative Examples 4 to 7).

Example 3, Comparative Examples 10 to 12

Induction of Differentiation from Human Osteoblast Cells to Bone Cells Under Serum-Free Conditions As in Example 1, to a glutamic acid-containing basal medium (DMEM), 5 µM of LPA, 1 mM of ascorbic acid 2-phosphate, 60 nM of selenide and 90 µM of glutamic acid were added to prepare a serum-free control medium (Comparative Example 10).

As in Example 1, to DMEM, 10 mM of β-glycerophosphate, 100 nM of dexamethasone and 200 µM of ascorbic acid phosphate, the concentrations being final concentrations, were added to prepare a bone cell differentiation-induction basal medium (differentiation basal medium). To this bone cell differentiation-induction basal medium, 5 µM of LPA, 1 mM of ascorbic acid 2-phosphate, 60 nM of selenide and 90 µM of glutamic acid were added to prepare a serum-free differentiation medium according to the present invention (Example 3).

As in Example 1, 10% of fetal bovine serum (FBS) was added to the basal medium and differentiation basal medium, respectively, to prepare a conventional medium (Comparative Example 11) and a conventional differentiation medium (Comparative Example 12).

Human osteoblasts (strain: normal human osteoblast (NHOst), available from LONZA) were plated in the wells of a 12-well culture plate to a cell population of 10,000 cells/cm$^2$, and the cells were cultured in each of these media at 37° C. under 5% CO$_2$ for 14 days, to induce differentiation into bone cells. Bone cells were confirmed by staining with alizarin red S.

Figure 5:
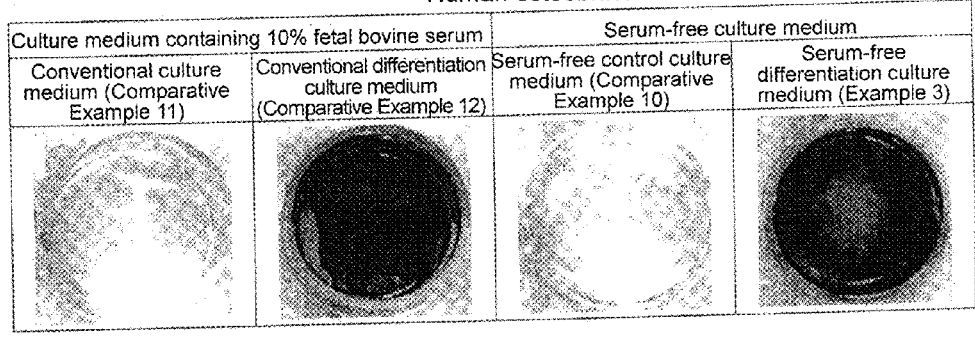
FIG. 5 shows the cells stained with alizarin red S, which cells were differentiation-induced into bone cells from mesenchymal stem cells originated from human bone marrow cells, in each of the media obtained in Example 3 and Comparative Examples 7 to 9 for 14 days.

The results are shown in FIG. 5. As shown in FIG. 5, by using the serum-free differentiation medium (Example 3), the bone cells grew to the same extent where the serum-containing conventional differentiation medium (Comparative Example 11) was used. On the other hand, with the serum-free control medium (Comparative Example 10) or the conventional medium (Comparative Example 11), bone cells were not induced.

The invention claimed is:

1. A method for inducing differentiation of mesenchymal stem cells into bone cells, the method, comprising:
   culturing mammalian mesenchymal stem cells in a serum-free culture medium capable of inducing the differentiation of the mammalian mesenchymal stem cells into bone cells, the serum-free culture medium comprising:
   a basal medium;
   an agent for inducing differentiation of mammalian mesenchymal stem cells into bone cells, wherein the agent comprises β-glycerophosphate, dexamethasone and vitamin C;
   a ligand for endothelial cell differentiation gene (Edg) family receptors in a concentration range of 0.01 µM to 50 µM, wherein the ligand is at least one selected from the group consisting of lysophosphatidic acid (LPA) and salts thereof, sphingosine 1-phosphate (S1P), and agonists for Edg family receptors; and
   selenium in a concentration range of 1 nM to 1 µM.

2. The method for inducing differentiation according to claim 1, further comprising at least one selected from the group consisting of melatonin, vitamin A, vitamin D, vitamin K and zinc.

3. The method for inducing differentiation according to claim 1, further comprising glutamic acid.

4. The method for inducing differentiation according to claim 1, wherein the basal medium is selected from the group consisting of DMEM, MEM alpha, MEM, Ham's F-12, RPMI-1640, DMEM/F12, William's medium E, MCDB medium, Medium 199, Fisher's medium, Iscove's modified Dulbecco's medium (IMDM), and McCoy's modified medium.

5. The method for inducing differentiation according to claim 1, wherein the agent for inducing differentiation simul-

SEQUENCE LISTING

```
<160> NUMBER OF SEQ ID NOS: 2

<210> SEQ ID NO 1
<211> LENGTH: 22
<212> TYPE: DNA
<213> ORGANISM: artificial
<220> FEATURE:
<223> OTHER INFORMATION: forward primer for amplifying alkaline
      phosphatase cDNA

<400> SEQUENCE: 1
cgtatttctc cagacccaga gg                                              22

<210> SEQ ID NO 2
<211> LENGTH: 22
<212> TYPE: DNA
<213> ORGANISM: artificial
<220> FEATURE:
<223> OTHER INFORMATION: reverse primer for amplifying alkaline
      phosphatase cDNA

<400> SEQUENCE: 2
ggccttgtcc tgaggagaaa ga                                              22
``` taneously contains β-glycerophosphate in a concentration range of 1 mM to 100 mM, dexamethasone in a concentration range of 1 nM to 1 μM, and vitamin C in a concentration range of 10 μM to 10 mM.

\* \* \* \* \*